(12) United States Patent
Zhang et al.

(10) Patent No.: US 10,470,675 B2
(45) Date of Patent: Nov. 12, 2019

(54) WIRELESS VIBROMETER WITH ANTENNA ARRAY

(71) Applicant: Wisconsin Alumni Research Foundation, Madison, WI (US)

(72) Inventors: Xinyu Zhang, Madison, WI (US); Teng Wei, Madison, WI (US); Shu Wang, Chicago, IL (US); Anfu Zhou, Beijing (CN)

(73) Assignee: Wisconsin Alumni Research Foundation, Madison, WI (US)

( * ) Notice: Subject to any disclaimer, the term of this patent is extended or adjusted under 35 U.S.C. 154(b) by 442 days.

(21) Appl. No.: 15/185,692

(22) Filed: Jun. 17, 2016

(65) Prior Publication Data

US 2017/0360317 A1    Dec. 21, 2017

(51) Int. Cl.
| | |
|---|---|
| *A61B 5/00* | (2006.01) |
| *A61B 5/024* | (2006.01) |
| *H04K 3/00* | (2006.01) |
| *A61B 5/05* | (2006.01) |
| *G01H 11/00* | (2006.01) |

(52) U.S. Cl.
CPC ............ *A61B 5/02444* (2013.01); *A61B 5/05* (2013.01); *G01H 11/00* (2013.01); *H04K 3/25* (2013.01)

(58) Field of Classification Search
None
See application file for complete search history.

(56) References Cited

U.S. PATENT DOCUMENTS

| | | | |
|---|---|---|---|
| 4,479,265 A | 10/1984 | Muscatell | |
| 2005/0220310 A1 | 10/2005 | McGrath | |
| 2010/0152600 A1* | 6/2010 | Droitcour | ................ A61B 5/05 600/534 |

\* cited by examiner

*Primary Examiner* — Christopher Koharski
*Assistant Examiner* — Elizabeth K So
(74) *Attorney, Agent, or Firm* — Boyle Fredrickson, SC

(57) ABSTRACT

A wireless vibrometer employs an antenna array to significantly boost the signal-to-noise ratio of faint received signals twin small objects vibrating at acoustic frequencies. This technique may be used to provide an improved physiological monitor (such as a pulse detector) or for long-range eavesdropping using the emitted power from a cell phone or the like.

14 Claims, 6 Drawing Sheets

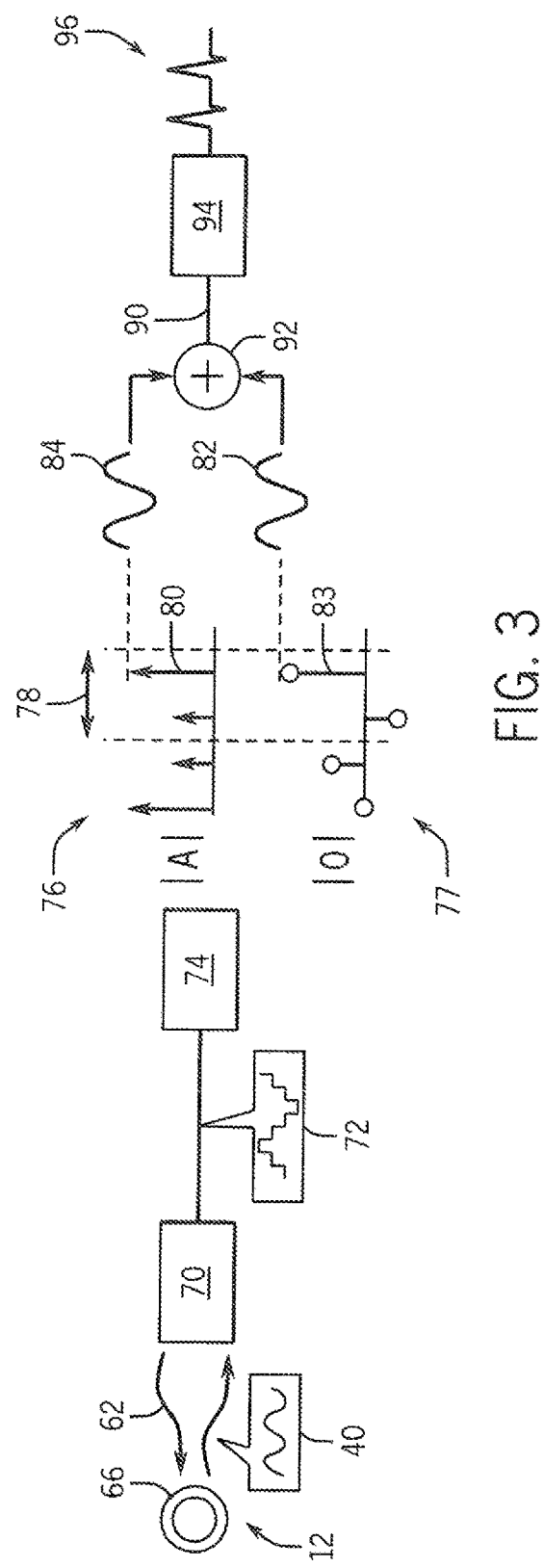

WIRELESS VIBROMETER WITH ANTENNA ARRAY

STATEMENT REGARDING FEDERALLY SPONSORED RESEARCH OR DEVELOPMENT

This invention was made with government support under CNS 1318292, CNS134,3363, CNS1350039, and CNS1404613 awarded by the National Science Foundation. The government has certain rights in the invention.

CROSS REFERENCE TO RELATED APPLICATION

- - -

BACKGROUND OF THE INVENTION

The present invention relates to methods of measuring acoustic signals, such as those produced by a person's pulse or voice, by using wireless signals, and in particular to a system using an antenna array for practical vibrometry in situations with small vibrating targets and/or weak signals.

Devices such as wrist mounted fitness monitors may monitor pulse by measuring changes in reflected light caused by blood flow (photoplethysmograhy). In each cardiac cycle, a pressure pulse distends the arteries slightly increasing reflective area of the blood. Accurate readings using photoplethysmograhy often requires repositioning the measuring device from the wrist to the forearm and securing it tightly about the forearm. Cold weather, tattoos, and irregular movements of the arm may interfere with measurements. Recently there has been some concern that photoplethysmography techniques can be inaccurate at high intensity workout levels.

SUMMARY OF THE INVENTION

The present invention provides a wireless vibrometer using an array of transmitters and receivers that may isolate and detect faint vibrations, for example, from an arterial wall during the cardiac cycle or from surfaces vibrating in response to speech.

In a fitness monitor, the array maybe directed inwardly from a wrist strap toward an artery and by isolating vibration of the artery walls may effectively measure pulse without interference from other physiological, movements and/or variations in the placement and contact of the array.

More generally the invention provides extremely sensitive measurement of the vibration of structures providing only weak reflections allowing a range of new applications of wireless vibrometry.

Specifically, in one embodiment, the invention provides a wireless vibrometer having an antenna array having antennas distributed over at least one dimension. A transmitter connectable to given antennas of the array shifts at least one of a relative phase and amplitude of a transmitter radiofrequency signal transmitted from each given antenna according, to a transmission weight associated with each given antenna. A receiver connectable to given antennas of the array, shills of at least one of a relative phase and amplitude of a reflection of the radiofrequency signal received from each given antenna according to a reception weight associated with each given antenna before, combining the reflection radiofrequency signals to a received signal. An electronic computer executes a program stored in a non-transitive medium to: (a) extract an audio signal from the received signal; (b) evaluate the audio signal to adjust the transmission weights and reception weights to provide a processed audio signal with improved signal-to-noise ratio; and (c) output, a measure of the processed audio signal.

It is thus a feature of at least one embodiment of the invention to provide improved measurement of small vibrating surfaces producing weak radiofrequency signals.

The vibrometer may include a housing for supporting the antenna array adjacent to a person's skin to direct transmitted radiofrequency signals into the skin and to receive reflection radio signals reflected out of the skin.

It is thus a feature of at least one embodiment of the invention to provide a physiological monitor overcoming the problems of, or supplementing, photoplethysmograhy.

The housing may provide an adjustable band for passing around the limb of a human to retain the housing against the It is thus a feature of at least one embodiment of the invention to provide a physiological monitor operable in the convenient form factor of an arm or wristband.

The electronic computer may extract a dominant frequency of the processed audio signal within a pulse rate range of the human heart and the measure of the processed audio signal is a pulse rate.

It is thus a feature of at least one embodiment of the invention to provide an improved pulse monitor.

The array may provide antennas dispersed in two dimensions.

It is thus a feature of at least one embodiment of the invention to permit a two-dimensional optimization of a synthesized measurement axis that can work with vibrating surfaces in a variety of orientations.

The antenna array may extend over an area of less than 2.5 square inches.

It is thus a feature of at least one embodiment of the invention to provide a compact wireless vibrometer suitable for portable devices.

The electronic computer may select the transmission weights and the reception weights by cycling through a limited set of discrete transmission weights and reception weights to select transmission weights and reception weights according to a maximization of the audio range of the received signal provided by the selected transmission weights and reception weights.

It is thus a feature of at least one embodiment of the invention to provide a method of beamforming when there is no a priori identified target.

The limited set of discrete transmission, weights and reception weights may provide for a range of amplitude weighting of no less than 2 to 1 in no more than 100 weights and/or a limited set of discrete transmission weights and reception weights to provide for a range of phase weighting of no less than 180 degrees in no more than 100 steps.

It is thus a feature of at least, one embodiment of the invention to employ a limited search space for tractable beamforming in this application.

The electronic computer may (I) transmit a radio signal from an antenna while cycling through a limited set of discrete transmission weights to select first transmission weights according to a maximization of the audio range of the received signal and then (ii) use the first transmission weights as reception weights while cycling through the limited set of discrete transmission weights to select second transmission weights according to a maximization of a measure of the audio signal of the received signal.

It is thus a feature of at least one embodiment of the invention to rapidly identify a dominant source for vibrometry.

The electronic computer may further control a frequency of the transmitter and receiver and cycles through a discrete set of transmission frequencies to select ,a transmission frequency for obtaining the extracted audio signal according to a maximization of a measure of the audio signal of the received signal.

It is thus a feature of at least one embodiment of the invention to provide improved sensitivity to faint vibrations through transmission frequency adjustment such as may accentuate radio signal interference effects.

In one embodiment, the invention may provide a system for eavesdropping on audio data, the system comprising a wireless transmitter (such as a cell phone) providing a microphone for receiving audio data and a transmitter for transmitting the audio data in an encrypted radio signal and a wireless vibrometer. The wireless vibrometer may include an antenna array having, antennas distributed over at least one dimension and a receiver connectable to given antennas of the array, the receiver receiving the encrypted radio signal at each given antenna and shilling at least one of a relative phase and amplitude of the reflection radiofrequency signal according to a reception weight associated with each given antenna before combining the reflection radiofrequency signals to a received signal. An electronic computer executes a program stored in a non-transitive medium to: (a) measure variations in electrical power of the encrypted radio signal over time; (b) extract an audio signal from the variations in electrical power; (c) measure the audio signal to adjust the transmission weights and reception weights to provide a processed audio signal with improved signal-to-noise ratio; and (c) output the processed audio signal.

It is thus a feature of at least one embodiment of the invention to provide a method of eavesdropping on encrypted radio transmissions by monitoring the vibration of the transmitter elements before signals from those vibrations have become encrypted.

In one embodiment, the invention provides a wireless transmitter hardened against eavesdropping and including (1) a microphone for receiving an audio signal to provide electrical audio data, (2) a transmitter for receiving electrical audio data, and (3) a power control signal, and transmitting the audio data in encrypted form at a power determined by the power control signal. An audio noise source provides an audio signal in the bandwidth of a human voice and communicates with the transmitter to provide at least a portion of the power control signal to the transmitter. The audio noise source provides a variation in transmitting power comparable to that produced without the audio noise source as a result of vibration of portions of the wireless transmitter under the influence of an audio signal.

It is thus a feature of at least one embodiment of the invention to produce a transmitter hardened against eavesdropping through monitoring of power variations caused by vibration of the elements of the transmitter.

These particular objects and advantages may apply to only some embodiments falling within the claims and thus do not define the scope of the invention.

BRIEF DESCRIPTION OF THE FIGURES

FIG. 3 is a signal processing diagram showing processing of a composite received radiofrequency signal to extract audio data;

DETAILED DESCRIPTION OF THE PREFERRED EMBODIMENT

Sensitive Vibrometry

Figure 1:
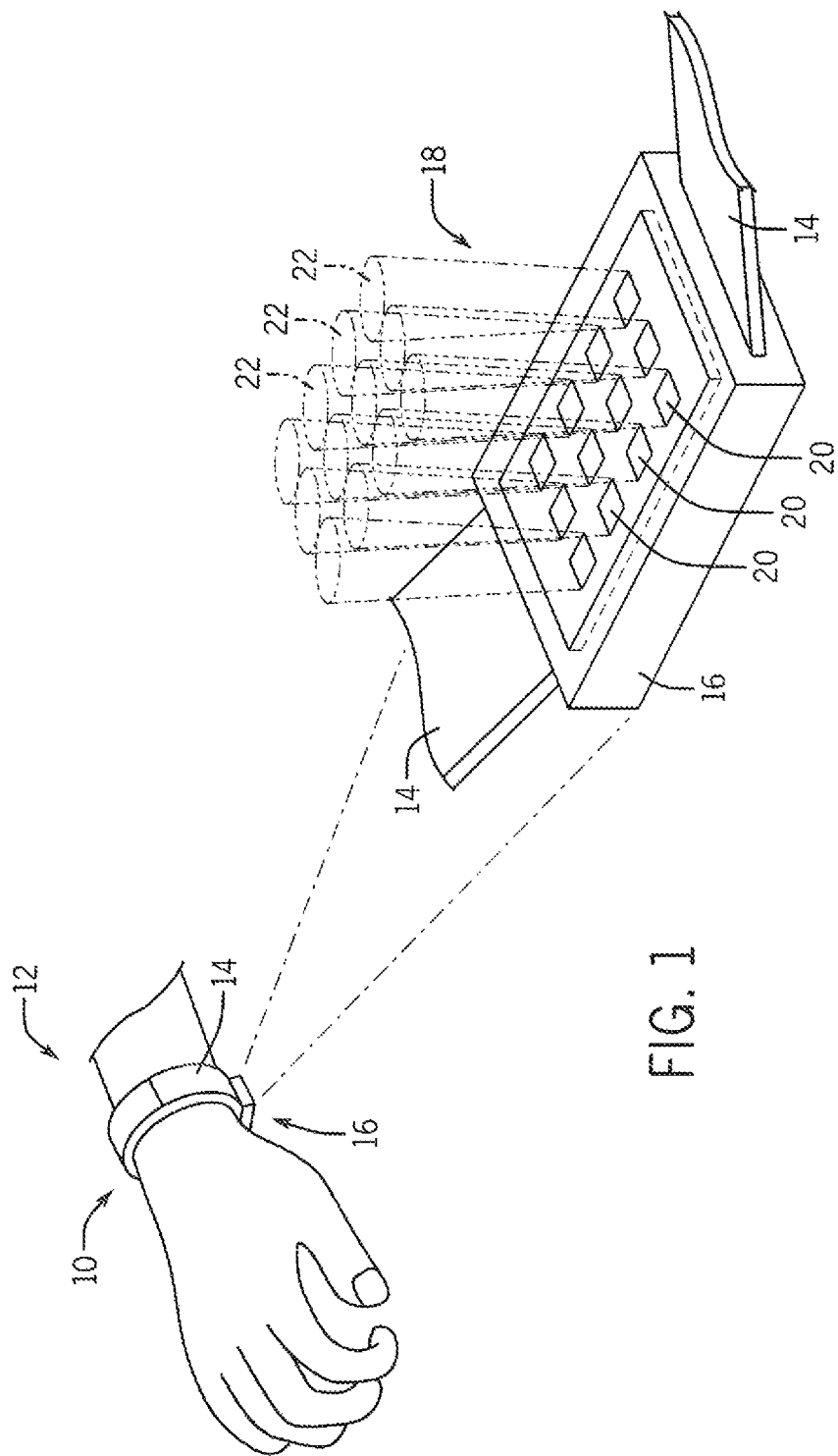
FIG. 1 is a perspective view of one embodiment of the invention directed to a wrist mounted physiological monitor held by a wristband and showing in an enlarged fragmentary phantom view, and antenna array such as may be held in position directed upward against the bottom of the wrist by the wristband.

Referring now to FIG. 1, in one embodiment, the invention may provide for a wristband 10 that may be placed about the wrist 12 or upper forearm of a person to monitor physiological signals manifest as vibration. Such signals may include cardiac pulse, respiration, hypovolemia and the like.

The wristband 10 may include a band portion 14, for example, constructed of an elastic material or including a hasp for tightening the band about the wrist 12. As so positioned, the band portion 14 may support housing 16 pressing upward, for example, against the underside of the wrist. The housing 16 may be substantially rigid and support an internal antenna array 18 of independent antennas 20. The antennas 20, for example, may be arranged in rows and columns in two dimensions, for example, limited to an area of approximately 2.5 inches or less so that the entire antenna array 18 may fit adjacent to the wrist.

The antennas 20 are located and constructed so as to direct or receive radiofrequency signals along primary lobe axes 22 directed to intersect the wrist 12 in a direction generally perpendicular to a plane of the array 18 over which the antennas 20 are dispersed.

Figure 2:
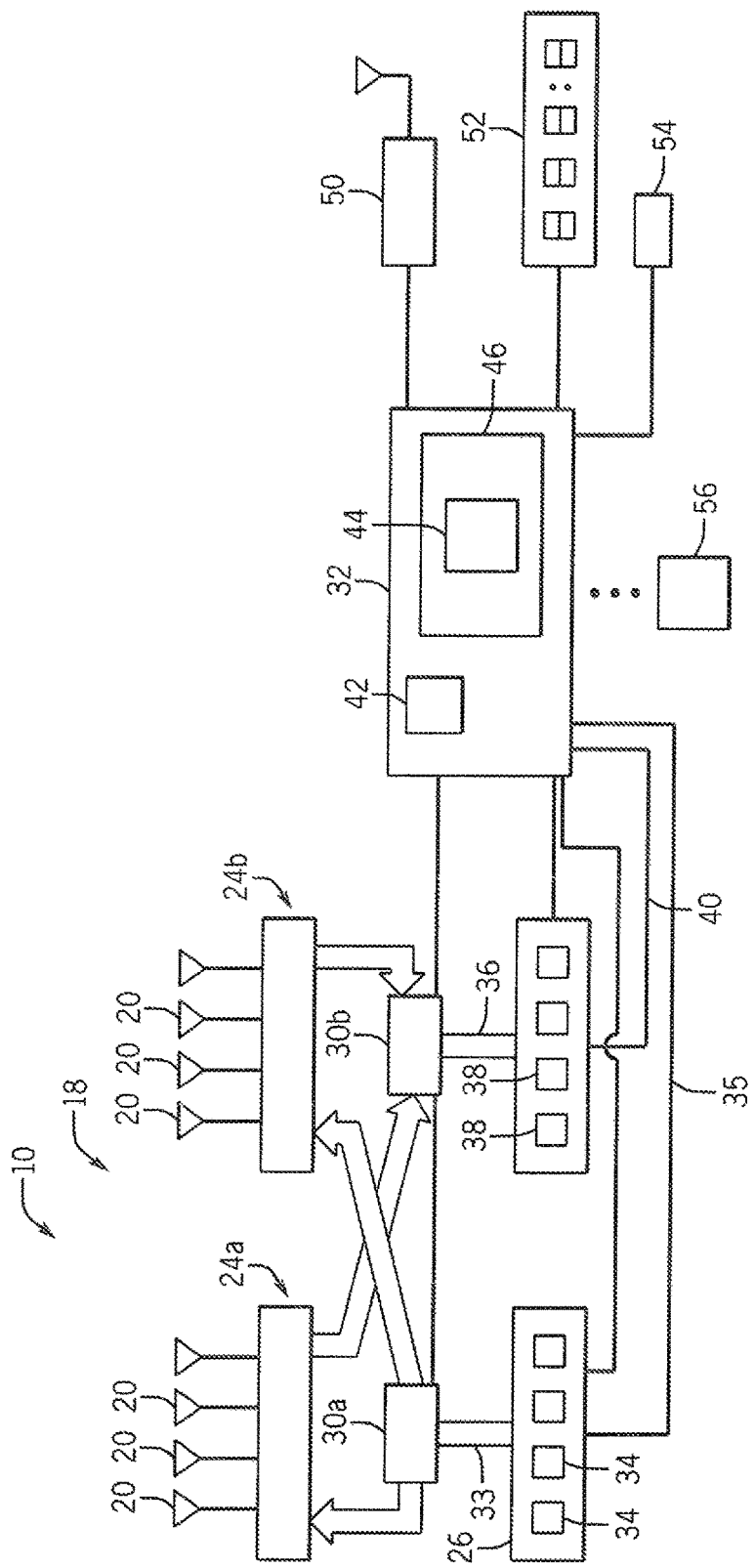
FIG. 2 is a block diagram of the electrical components of the embodiment of FIG. 1 showing circuitry for switching weighted transmission and reception signals between antennas of the array of FIG. 1 through the use of an electronic computer.

Referring now to FIG. 2, the antennas 20 can be divided into separate groups 24a and 24b, either of which may be used for transmission and reception as will be discussed. The groups 24a and 24b will generally include interspersed antennas 20 to provide maximum spatial separation among antennas 20 in each antenna group 24.

Antennas 20 in each antenna group 24a and 24b may be connected either to a transmitter 26 or a receiver 28 and this connection may be switched by means of multiplexers 30a and 30b under the control of a computer 32 as will be discussed.

Transmitter 26 provides a set of output signals 33 based on a common transmission signal 35 but independently shifted in at least one of phase and amplitude with respect to that common transmission signal 35 according to transmission weights 34. The values of the transmission weights 34 may be controlled by the computer 32 and will be determined by a process described below. Each of these separately shifted output signals 33 is provided to a corresponding different antenna 20 in the antenna group 24a or 24b, whichever is associated with the transmitter 26.

In a similar manner, receiver 28 may receive a set of input signals 36 from antennas 20 of a selected one of antenna group 24a and 24b. These input signals 36 may then be independently shifted in at least one of phase and amplitude according to reception weights 38 (also controlled by the computer 32 as will be discussed). The shifted input signals 36 may then be combined to produce a received radio signal 40.

In one embodiment, the transmitter 26 and receiver 28 may operate in at a set of frequencies within a range falling within a broader range of 300 megahertz to 64 gigahertz, although the invention in some embodiments need not be limited to this frequency range.

The common transmission signal 35 may be generated by the computer 32, and as noted above, the computer 32 may control the transmission weights 34 (for example, describing a frequency and amplitude or a spectral content). In addition, the computer 32 may receive a combined radio signal 40, for example, after basic demodulation and downshifting or directly as sample data by a high-speed analog-to-digital converter and as noted above may control the reception weights 38.

The computer 32, as is generally understood in the art, may include one or more processors 42 executing a stored program 44 held in computer memory 46. The computer 32 may communicate with a secondary transmitter 50, for example, a Bluetooth transmitter, for communicating data to a cell phone or the like, and to a display 52 and user controls 54 such as pushbuttons and the like to provide an interface to a user, for example, for receiving commands and displaying output value such as pulse rate and the like.

Each of the circuit elements described above may be contained within the housing 16 and may be powered by means of a self-contained battery 56 as is generally understood in the art.

Referring now to FIG. 3, generally the program 44 will control the computer 32 and through the computer 32 control the other components connected to the computer 32 in order to transmit a signal 62 from the antennas 20 being the signal 33 transmitted from each of the antennas 20. Similarly, the computer 32 may receive signal 40 from the antennas 20 as combined by the receiver 28 being a signal reflected from tissue 66 such as an arterial wall in the wrist 12.

The receive signal 40 may be sampled and converted to digital values by an A/D converter 70 at a high sampling rate well above the Nyquist sampling rate needed for the audio upper range of the vibration of interest. For a pulse rate of 0.5 hertz to 2.5 hertz, the sampling rate will be in excess of 1 megahertz, well above the Nyquist sampling rate of five hertz. As will be discussed later, when the invention is used for decoding human speech, the range of vibration of interest may be, for example, in a range of 80-500 hertz. For human speech, therefore, the sampling rate is still well above the Nyquist sampling rate necessary to sample human speech.

Excess sampling by the A/D converter 70 may allow averaging or other combinations of adjacent samples to provide a lower sample rate signal 72 having improved noise qualities.

Signal 72 may then be transformed, for example, by a fast Fourier transform 74 implemented in software or hardware to provide a dynamic frequency domain signal including amplitude signal 76 and phase signal 77 as is generally understood in the art. The amplitude signal 76 and phase signal 77 may be "windowed" to remove "DC" components and other values outside of the frequency range 78 being a frequency range of interest, for example, 0.5 hertz to 2.5 hertz for pulse rate or 80 hertz to 500 hertz for intelligible vocal communication. This windowed frequency domain signal may then be inverse transformed to provide an extracted or demodulated audio signal. Alternatively, and in the preferred embodiment, a peak amplitude component 80 of the amplitude signal 76 may be amplitude demodulated to produce an audio signal 82 and/or a peak component of the phase signal 83 corresponding to the peak amplitude component 80 and may be phase demodulated to produce audio signal 84. Either of these signals 82 and 84 may be used individually or they may be combined as indicated by adder 90 to provide a measured audio signal 92.

For extracting pulse rate, this measured audio signal 92 may be further processed by a post-processor 94 according to the signal of interest. For example, for pulse rate, the post-processor 94 may provide a band pass filter and frequency counter that may output a pulse rate signal 96 that may be displayed on the display 52 in FIG. 2 and/or transmitted on the transmitter 50 to a remote display. When the signal of interest is human speech, post-processor 94, for example, may provide amplification gain control and the like and other intelligibility enhancing filtration steps generally understood in the art.

Each of the components of the Fourier transform 74, the adder 90, and the post-processor 94 may be implemented in software or hardware according to techniques well known in the art.

Figure 4A:
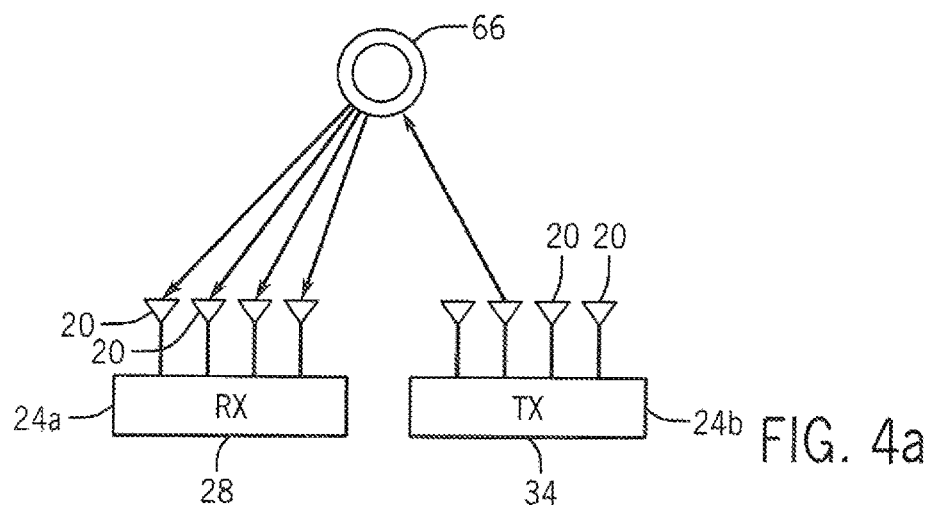
FIGS. 4a-4c are simplified views of the antenna array of FIG. 2 showing steps in establishing the weighted values of the transmission and reception signals.
Figure 4B:
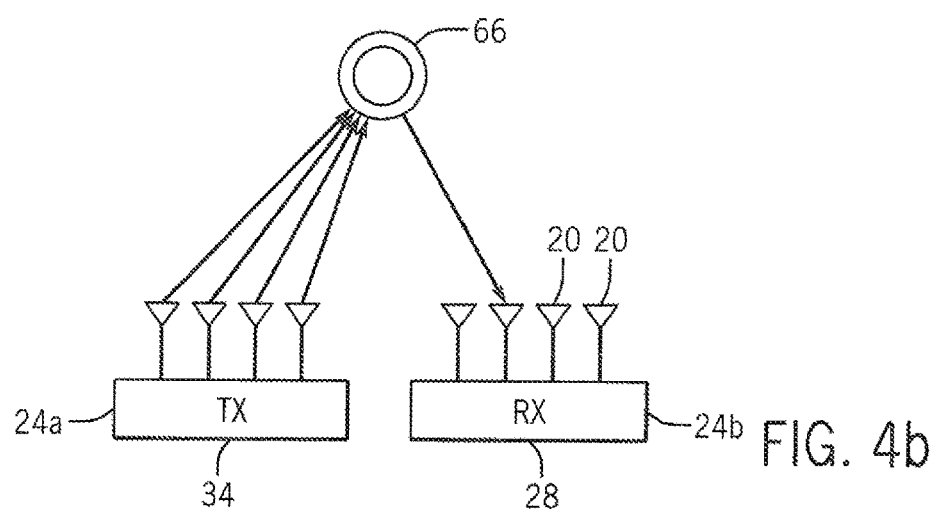
Figure 4C:
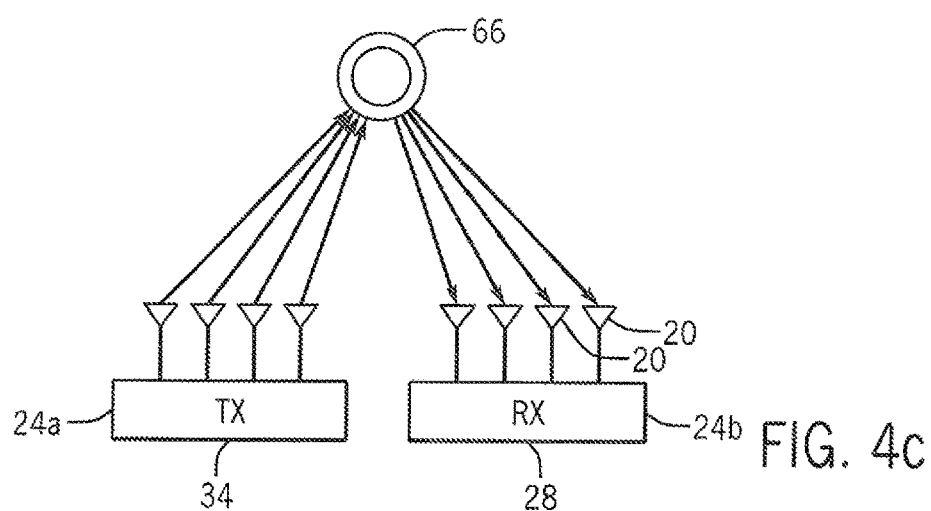
Figure 5:
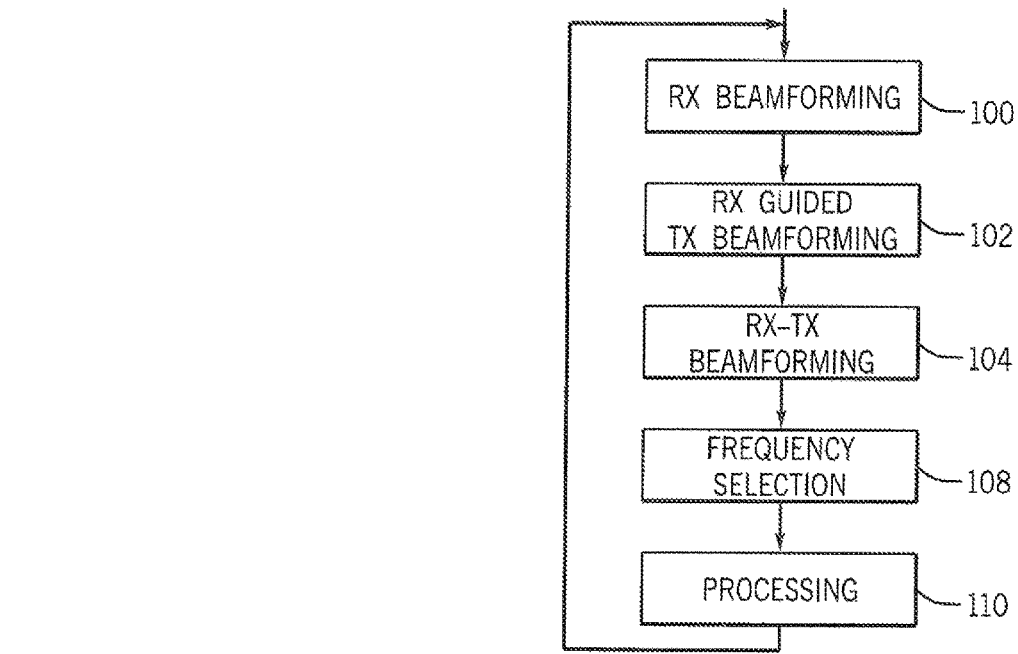
FIG. 5 is a flowchart of a program executed by the computer FIG. 2 in implementing the weight-determining steps of FIG. 4.

Referring now to FIGS. 4 and 5, the signal 40 processed as described above will normally be relatively weak because of the small reflection area of the tissue 66. In addition, this week signal maybe corrupted by motion artifacts, for example, in the contact between the housing 16 and the skin and by movement of tendons and muscles around the tissue 66 of interest. Accordingly, the present invention may perform a "blind" beamforming to increase signal specificity with respect to the tissue 66.

Referring now to FIGS. 2 and 4a and two process blocks 100 of FIG. 5, a first step in this beamforming process determines reception weights 38 by connecting the transmitter 26 to an arbitrary single antenna 20 of antenna group 24b and transmitting a carrier signal, for example, a constant frequency carrier signal having a frequency much higher than the bandwidth of the expected audio signal 92. At the same time, receiver 28 is connected to antenna group 24a and each antenna 20 in antenna group 24a receives a signal which is processed by the receiver 28 using, corresponding reception weights 38.

These reception weights 38 may be, set initially to an arbitrary value (for example, 0 phase shifting, and an amplification factor of 1) and then the reception weights 38 are sequenced through discrete steps of one or both of amplitude and phase. For example, the reception weights 38 may range from 0.5 to 2 covering plus and minus 3 db of magnitude range in steps of 0.05. More generally, the reception weights 38 may have a range of amplitude weighting, of no less than 2 to 1 and the set of reception weights 38 may be less than 100 weight values for each reception weight 38. Alternatively or in addition, the reception weights 38 may step through a range of phase shifts of 0-2π in steps of 0.1. More generally, the reception weights 38 may provide for phase weighting of no less than 180 degrees and the set of different weight values for each reception weight 38 is less than 100 steps. These same ranges and step numbers will also apply to sequencing through the transmission weights 34 as will be described below.

The reception weights 38 are evaluated by extracting the audio signal 92 (shown with respect to FIG. 3) and evaluating a signal-to-noise measure (such as peak signal-to-noise ratio). Generally the reception weights 38 are selected to maximize the signal-to-noise ratio measurement.

Although, it is possible to search through all possible combinations of the discretized reception weights 38, one embodiment of the invention employs a greedy algorithm in which each reception weight 38 is set in sequence, and the proper setting of the next reception weight 38 in the sequence is evaluated as to whether it improves the signal-to-noise ratio (for example, a peak signal-to-noise ratio) existing for the previously determined reception weights 38 without changing those previously determined reception weights 38.

Once reception weights 38 have been determined, these reception weights 38 are used as the transmission weights 34 for the same antennas 20 of antenna group 24a which is now connected to the transmitter 26 (switched from the receiver 28) as shown in FIG. 4b. The transmitter 26 operating through antennas 20 of the antenna group 24a can be assumed to have provided beamforming to the location of the tissue 66 of interest based on the reciprocity in the behavior of constructive and destructive interference in both transmission and reception of radio signals.

The common transmission signal 35 previously transmitted through one of antenna group 24b is now transmitted through each antenna 20 of antenna group 24a as subject to the transmission weights 34 as shown in FIG. 4b and as indicated by process block 102 of FIG. 5. Reception weights 38 are again determined for the antennas 20 of antenna group 24b using the process described above with respect to determining reception weights 38, again, to maximize the measure of signal-to-noise ratio received at the multiple antennas 20 of antenna group 24b.

Once this process is completed and as indicated by process block 104 of FIG. 5 and FIG. 4c, the antenna banks 24a and 24b are operated simultaneously (antenna group 24a receiving output from the transmitter 26 and antenna group 24b providing input to the receiver 28) using the derived transmission weights 34 and reception weights 38.

Using these derived transmission weights 34 and reception weights 38, at optional step 108, different frequencies are used for the carrier frequency to determine a frequency that maximizes the measure of signal-to-noise ratio used in the determination of the transmission weights 34 and reception weights 38.

As indicated by process block 110, the identified transmission weights 34, reception weights 38 and carrier frequency are then used to collect signal 40 for processing to extract an audio signal 92 and provide a measurement of that audio signal in signal 96.

Figure 6:
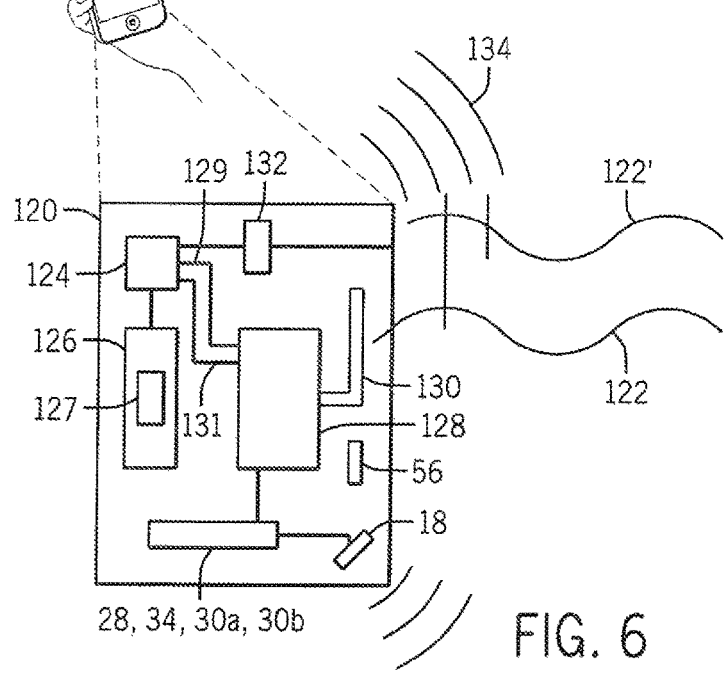
FIG. 6 is a perspective view and block diagram of the principal components of a handheld radio transmitter such as a cell phone showing phase/amplitude modulation caused by vibration of the phone and/or its components.
Figure 9:
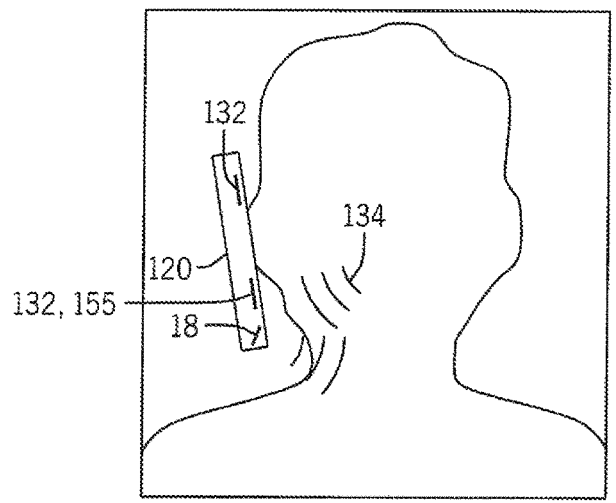
FIG. 9 is a figure showing an alternative embodiment of placement of the antenna array of FIG. 1 for augmenting vocal communications in noisy environments.

Referring now to FIGS. 1, 6 and 9, the ability to extract audio signals from small vibrating reflectors per the present invention makes possible the use of the array 18 and the above described circuitry and processing as an auxiliary audio pick up, for example, for a cell phone 120. In this embodiment, the array 18 may be incorporated into the cell phone 120 to direct a radiofrequency signal 62 (shown in FIG. 3) toward a user's throat (for example) to extract a voice signal in the manner of a throat microphone. This voice signal may be used instead of or to augment, audio signals 134 received by a microphone 155 thus allowing the cell phone 120 to be better used in highly noisy environments.

Encryption Bypassing

Referring to FIG. 6, the sensitivity provided by the present invention raises the possibility of eavesdropping on radio transmitters even when the transmitters encrypt the transmitted data. A typical radio transmitter such as a cell phone 120 may transmit a radio signal 122 containing encrypted data, for example, transmitted in a packet format with the data of each packet encrypted.

As is generally understood in the art, the cell phone 120 may include a processor 124 communicating with a memory 126 holding a stored program 127. The processor 124 may provide encrypted data signals 129 to a transceiver 128 for transmission as radio signals 122 through an antenna 130. The processor 124 may also control the transmitter transmission power through a power control signal 131 to the transceiver 128.

The cell phone 120 may also include acoustically driven movable elements 132 such, as a speaker. Such elements are constructed to vibrate to provide audio output of received conversations. During this vibration, the movable element 132 will mechanically communicate vibrations to the antenna 130 to produce a phase shifted radio signal 122 emanating directly from the antenna 130. The amount of phase shifting will depend on the instantaneous movement of the element 132 driven by the audio signal 134. In addition, constructive and destructive interference between radio signal 122 and reflection signal 122' in the environment will cause fluctuations in the power of a received composite of radio signal 122 and reflection signal 122' that may be detected by the present invention.

Figure 7:
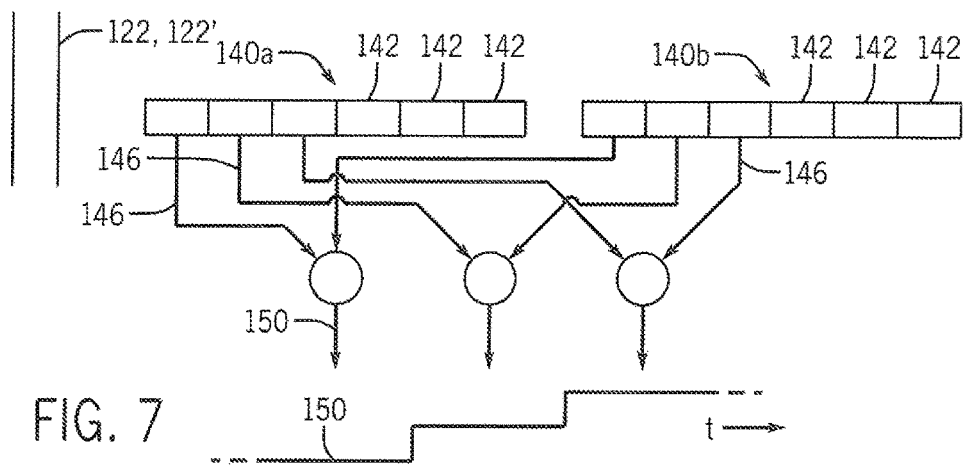
FIG. 7 is a diagram of a processing step that may be implemented by the processor of FIG. 2 to measure variations in transmitted power level in packets transmitted by the transmitter of FIG. 6 to extract audio data.

Referring now to FIG. 7, specifically, the composite radio signal 122 and reflection signal 122' may provide for successive packets 140a and 140b each containing multiple symbols 142, for example, in a pulse code modulated constellation. Standard circuitry on the transceiver 128 may extract the radiofrequency power represented by each symbol 142 as power signals 146. The power signals 146 for corresponding symbols 142 of successive packets 140 are then compared to provide a corresponding set of power delta signals 150 that may accurately track constructive and destructive interference of the radio signal 122 and reflection signal 122' as manifest in the changing amplitude of the combined signal which reveals motion of the movable elements 132. The corresponding symbols 142 need not be in the same order in each packet 140a and 140b (as shown) but may be selected so that only identical symbols are compared. By comparing identical symbols, the high variation in power as a function of symbol is accommodated.

To the extent that the packets 140 do not arrive at regular intervals, the delta signals 150 may be interpolated to regular sampling intervals.

This delta signal 150 may then be processed in the same manner as signal 64 of FIG. 3 using the blind beamforming steps 100-110 of FIG. 5 to determine the appropriate transmission weights 34 and reception weights 38. A potentially long range eavesdropping is provided because of the high signal strength of radio signal 122 compared to a reflected signal 122' as provided in the example of FIG. 3.

Figure 8:
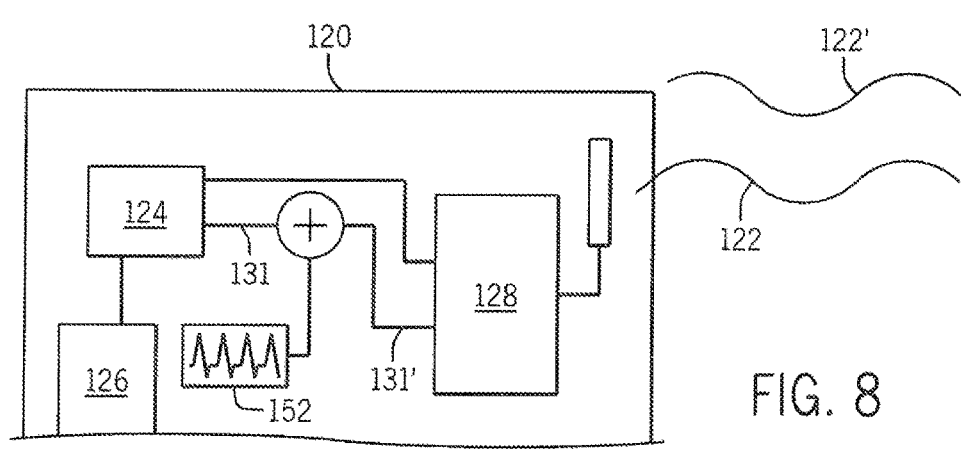
FIG. 8 is a fragmentary view of the transmitter of FIG. 6 including additional components to prevent eavesdropping through the use of the technique of FIG. 7.

Referring now to FIG. 8, this possibility of eavesdropping may be decreased through modification of the cell phone 120 by introduction of a noise component into the power control signal 131 that masks amplitude changes caused by vibration of the movable element 132. In particular, the power control signal 131 from the processor 124 may be summed to a noise source 152, for example, the latter producing pseudorandom noise having a power spectrum concentrated in the band of human speech. A modified power control signal 131' is then provided to the transceiver 128 to control the power level at which each packet 140 is transmitted. The resulting power fluctuations in the radio signal 122 serve to mask power fluctuation caused by the reflection signal 122'.

This application incorporates by reference the paper: "Acoustic Eavesdropping through Wireless Vibrometry" by Teng Weiy, Shu Wangy, Anfu Zhou and Xinyu Zhangy MobiCom'15, Sep. 7-11. 2015, Paris, France ACM 978-1-4503-3619-2/15/09.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features, The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. it is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

The invention claimed is:

1. A wireless vibrometer comprising:
    an antenna array having antennas distributed over at least one dimension;
    a transmitter connectable to given antennas of the array, the transmitter transmitting a transmitter radiofrequency signal and shifting at least one of a relative phase and amplitude of the transmitter radiofrequency signal transmitted from each given antenna according to a transmission weight associated with each given antenna, the shifting being manifest in the transmitter radiofrequency signal as it is transmitted;
    a receiver connectable to given antennas of the array, the receiver receiving a reflection of the radiofrequency signal from the array and shifting at least one of a relative phase and amplitude of a reflection of the radiofrequency signal after receipt of the radiofrequency signal from each given antenna according to a reception weight associated with each given antenna before combining the reflection radiofrequency signals to a received signal; and
    an electronic computer executing a program stored in a non-transitive medium to:
    (a) extract an audio signal from the received signal;
    (b) evaluate the audio signal to adjust the transmission weights and reception weights to provide a processed audio signal with improved signal-to-noise ratio; and
    (c) output a measure of the processed audio signal.

2. The wireless vibrometer of claim 1 further including a housing for supporting the antenna array adjacent to a person's skin to direct transmitted radiofrequency signals into the skin and to receive reflection radio signals reflected out of the skin.

3. The wireless vibrometer of claim 2 wherein the housing provides an adjustable band for passing around a limb of a human to retain the housing against the limb.

4. The wireless vibrometer of claim 3 wherein the electronic computer extracts a dominant frequency of the processed audio signal within a pulse rate range of the human heart and the measure of the processed audio signal is a pulse rate.

5. The wireless vibrometer of claim 4 wherein the array provides antennas dispersed in two dimensions.

6. The wireless vibrometer of claim 5 wherein the antenna array extends over an area of less than 2.5 square inches.

7. The wireless vibrometer of claim 1 wherein the electronic computer selects the transmission weights and the reception weights by cycling through a limited set of discrete transmission weights and reception weights to select transmission weights and reception weights according to a maximization of the audio range of the received signal provided by the selected transmission weights and reception weights.

8. The wireless vibrometer of claim 7 wherein the limited set of discrete transmission weights and reception weights provides for a range of amplitude weighting of no less than 2 to 1 in no more than 100 weight increments.

9. The wireless vibrometer of claim 7 wherein the limited set of discrete transmission weights and reception weights provides for a range of phase weighting of no less than 180 degrees in no more than 100 weight increments.

10. The wireless vibrometer of claim 1 wherein the electronic computer:
  (i) transmits a radio signal from an antenna while cycling through a limited set of discrete transmission weights to select first transmission weights according to a maximization of the audio range of the received signal; and
  (ii) uses the first transmission weights as reception weights while cycling through the limited set of discrete transmission weights to select second transmission weights according to a maximization of a measure of the audio signal of the received signal.

11. The wireless vibrometer of claim 10 wherein the measure of the audio signal is a measure of signal-to-noise ratio.

12. The wireless vibrometer of claim 1 wherein the electronic computer further controls a frequency of the transmitter and receiver and cycles through a discrete set of transmission frequencies to select a transmission frequency for obtaining the extracted audio signal according to a maximization of a measure of the audio signal of the received signal.

13. The wireless vibrometer of claim 12 wherein the measure of the audio signal is a measure of signal-to noise ratio.

14. The wireless vibrometer of claim 1 wherein the frequency of the transmitter and receiver is selected from a frequency range of 500 megahertz to five gigahertz.

\* \* \* \* \*